(12) United States Patent
Lee et al.

(10) Patent No.: US 8,211,465 B2
(45) Date of Patent: Jul. 3, 2012

(54) IMMEDIATE RELEASE AND SUSTAINED RELEASE IBUPROFEN DOSING REGIMEN

(75) Inventors: Der-Yang Lee, Flemington, NJ (US); Frank Bunick, Randolph, NJ (US); James Schwing, Cherry Hill, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/367,504

(22) Filed: Feb. 7, 2012

(65) Prior Publication Data

US 2012/0136060 A1    May 31, 2012

Related U.S. Application Data

(63) Continuation of application No. 11/839,168, filed on Aug. 15, 2007, now Pat. No. 8,137,694.

(51) Int. Cl.
*A61K 9/22* (2006.01)
*A61K 31/19* (2006.01)

(52) U.S. Cl. ........................ 424/468; 514/570

(58) Field of Classification Search .................. 424/468; 514/570
See application file for complete search history.

(56) References Cited

U.S. PATENT DOCUMENTS

| | | |
|---|---|---|
| 4,279,926 A | 7/1981 | Bruzzese et al. |
| 4,873,231 A | 10/1989 | Smith |
| 5,424,075 A | 6/1995 | Daher et al. |
| 5,510,385 A | 4/1996 | Stroppolo et al. |
| 6,004,582 A | 12/1999 | Faour et al. |
| 6,183,778 B1 | 2/2001 | Conte et al. |
| 6,753,009 B2 | 6/2004 | Luber et al. |
| 8,137,694 B2 * | 3/2012 | Lee et al. ........... 424/468 |
| 2004/0186180 A1 | 9/2004 | Gelotte et al. |

FOREIGN PATENT DOCUMENTS

| | | |
|---|---|---|
| CN | 1758904 A | 4/2006 |
| EP | 255002 A | 2/1988 |
| WO | WO 95/01781 A | 1/1995 |
| WO | WO 96/41617 A | 12/1996 |

OTHER PUBLICATIONS

Lopes et al: "Compressed mini-tablets as a biphasic delivery system" International Journal of Pharmaceutics, Amsterdam, NL, vol. 323, No. 1-2, Oct. 12, 2006, pp. 93-100, XP005658498 ISSN: 0378-5173.
Maggi et al: "Formulation of Biphasic release tablets containing slightly soluble drugs" European Journal of Pharmaceutics and Biopharmaceutics, Elsevier Science Publishers B.V., Amsterdam, NL, vol. 48, No. 1, Jul. 1999, pp. 37-42, XP000834476 ISSN: 0939-6411.
Martin W. et al., "Pharmacokinetics and Absolute Bioavailability of Ibuprofen After Oral Administration of Ibuprofen Lysine in Man", Biopharmaceutics & Drug Disposition, (1990), pp. 265-278, vol. 11.
Palmisano G.P. et al., "Double-Blind Crossover Comparison of Ketoprofen, Ibuprofen, and Placebo in the Treatment of Patients with Primary Dysmenorrhea", Advances in Therapy, Jul./Aug. 1988, pp. 128-137, vol. 5, No. 4.

* cited by examiner

*Primary Examiner* — Aradhana Sasan
(74) *Attorney, Agent, or Firm* — Laura A. Donnelly

(57) ABSTRACT

A method of administering non-steroidal-anti-inflammatory drugs, in particular propionic acid derivatives such as ibuprofen, is provided. The inventive dosage forms provide an initial release of the NSAID and a second sustained release of NSAID, preferably in a single dosing step.

6 Claims, 4 Drawing Sheets

IMMEDIATE RELEASE AND SUSTAINED RELEASE IBUPROFEN DOSING REGIMEN

This application is a continuation of U.S. Ser. No. 11/839,168 filed on Aug. 15, 2007, now U.S. Pat. No. 8,137,694, the complete disclosure of which is hereby incorporated herein by reference for all purposes.

The present invention relates to a novel dosing regimen for non-steroidal anti-inflammatory drugs, particularly propionic acids. This dosing regimen provides sustained therapeutic effect over extended time periods.

BACKGROUND OF THE INVENTION

Therapeutic agents for treating pain, inflammation, and fever include analgesics, anti-inflammatories, and antipyretics. Non-steroidal anti-inflammatory drugs (NSAID's) are one type of such therapeutic agents. They include propionic acid derivatives, acetic acid derivatives, fenamic acid derivatives, biphenylcarbodylic acid derivatives, oxicams, and cyclooxygenase-2 (COX-2) selective NSAID's.

Propionic acids include for example ibuprofen, naproxen, and ketoprofen. Ibuprofen in particular is a widely used, well known NSAID possessing analgesic and antipyretic properties. Ibuprofen is chemically known as 2-(4-isobutylphenyl)-propionic acid. It has been commercially available as an over-the-counter drug in many forms for several years.

NSAID's are typically administered on a once to four times daily basis, with the daily dose ranging from about 50 to about 2000 milligrams, preferably from about 100 to 1600 and most preferably from about 200 to about 1200 milligrams.

It is known to administer NSAID's and other drugs in multiple doses over 12 or 24 hours. For example, it is known to administer multiple doses containing equal amounts of ibuprofen over 12 to 24 hours. Sustained release dosage forms containing ibuprofen are also known.

Palmisano et al., *Advances in Therapy*, Vol. 5, No. 4, July/August 1988 reports on a study of ketoprofen and ibuprofen for treating primary dysmenorrhea. This reference discloses the use of multiple doses of ketoprofen (initial dose of 150 mg followed by subsequent doses of 75 mg) and ibuprofen (initial dose of 800 mg followed by subsequent doses of 400 mg).

A double-blind, randomized, parallel, placebo-controlled, single center, PK/PD dental pain study was conducted over a 12 hour observation period to evaluate the pharmacokinetic, pharmacodynamic, efficacy and safety profiles of certain ibuprofen dosing regimens. Specifically, a single dose of 600 mg ibuprofen extended release caplets was compared with equivalent total doses of ibuprofen immediate release 200 mg caplets administered in three different dosing regimens as well as placebo in the treatment of moderate to severe postoperative dental pain. The ibuprofen was administered as ibuprofen extended release 600 mg caplets or one or more ibuprofen immediate release 200 mg caplets. One sub-group of patients had both pharmacokinetic and pharmacodynamic evaluation (PK group). The other sub-group of patients had only the analgesic efficacy evaluations (non-PK group). Patients from both subgroups were assigned at random to one of the five following treatments:

| | |
|---|---|
| Ibuprofen Extended Release | 600 mg single dose at 0 hour |
| Ibuprofen Immediate Release | 600 mg single dose at 0 hour |
| Ibuprofen Immediate Release | 400 mg at 0 hour; 200 mg at 4 hours |
| Ibuprofen Immediate Release | 200 mg at 0, 4, and 8 hours |
| Placebo | |

Patients' assessments of pain intensity and pain relief as well as blood samples for plasma ibuprofen analysis were obtained at the study site at hours 0, 0.25, 0.5, 1, 1.5, 2, 2.5, 3, 4, 4.5, 5, 6, 7, 8, 8.5, 9, 10, 11 and 12. A stopwatch technique was used to measure the onset of meaningful pain relief. The study found that the 400/200/0 administration of ibuprofen provided excellent pain relief over the entire 12-hour study period. During the first four hours, the 400/200/0 treatment, along with the 600/0/0 immediate release treatment, provided superior pain relief over the other treatments. During the 4 to 12 hour interval, the 400/200/0 treatment alone provided the highest pain relief scores, despite the fact that no further ibuprofen was administered after the first four hours.

Applicants have now discovered that ibuprofen can be provided to a mammal, preferably a human, in a specific single dosing step to achieve improved therapeutic effect, especially pain relief, compared with known dosing regimens and in a more convenient/compliant dose form. In particular, ibuprofen is provided to the mammal, in one dosage form to provide an initial immediate release dose followed by a delayed second sustained release dose of ibuprofen. No further dosings are required to provide a $C_{min}$ of 5-10 mcg/mL for a period of at least about 8 hours after administration of the dosage form.

SUMMARY OF THE INVENTION

The invention provides a method of administering an NSAID, which consists of providing to a mammal in a single dosing step an initial dose of said NSAID and a delayed second sustained release dose of said NSAID, said NSAID from the immediate release and the sustained release portions of the dosage form have a duration of 8 hours, more preferably at 10 hours, most preferably 12 hours.

The invention also provides a method of administering a propionic acid derivative to a mammal, over a 12-hour time period, which comprises providing a first peak plasma concentration of said propionic acid derivative of about 10 to about 30 mcg/mL in said mammal about 30 to about 120 minutes after said initial dose, and a second plasma concentration following the first peak plasma concentration of said propionic acid derivative of at least about 10 mcg/mL for up to about 6 hours, preferably up to about 8 hours after administration of said initial dose.

In one embodiment, the invention also provides a method of administering in a single dosing step a propionic acid derivative, which comprises providing to a mammal, over a 12 hour time period, an initial dose of said propionic acid derivative at the beginning of said 12 hour time period, followed by a second sustained release dose of said propionic acid derivative about 2 to about 10 hours after administration of said initial dose, said initial dose load of propionic acid derivative being at least about twice the dose load of propionic acid derivative in said second dose, wherein no further propionic acid derivative is provided during said 12 hour time period.

DETAILED DESCRIPTION OF THE INVENTION

Figure 1:
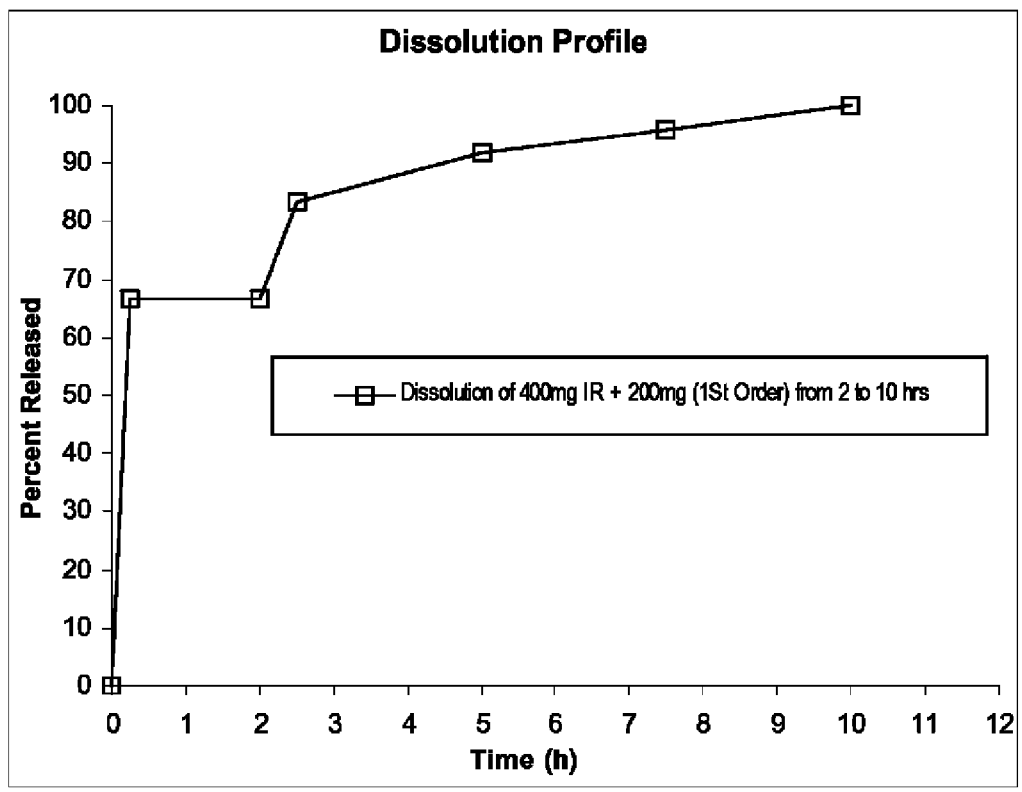
FIGS. 1A and 1B depict ibuprofen dissolution profile and absorption levels as a function of time for the dosing regimen reported in Example 1.
Figure 1B:
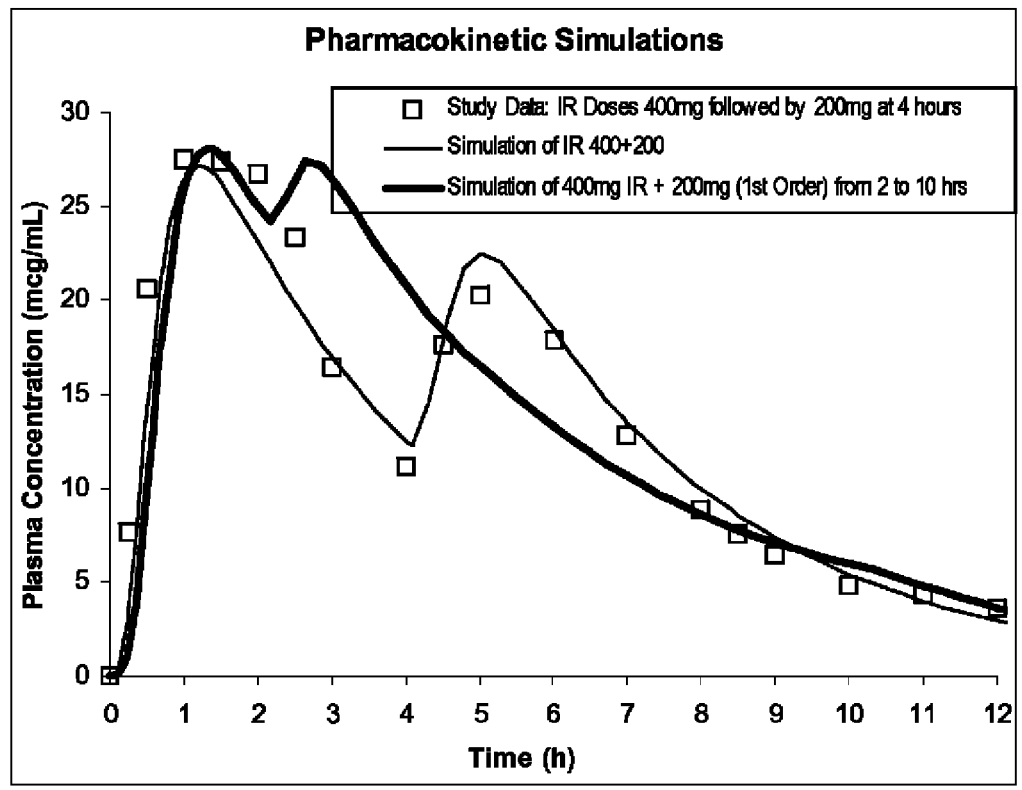
Figure 2:
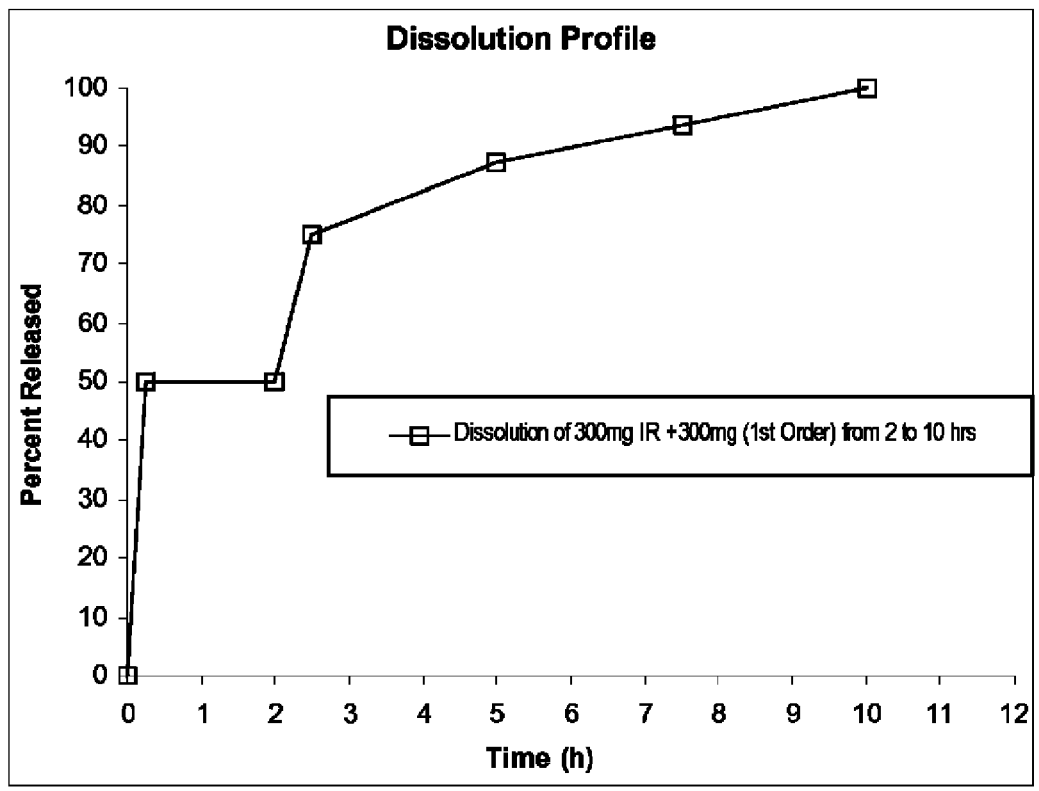
FIGS. 2A and 2B depict ibuprofen dissolution profile and absorption levels as a function of time for the dosing regimen reported in Example 2.
Figure 2:
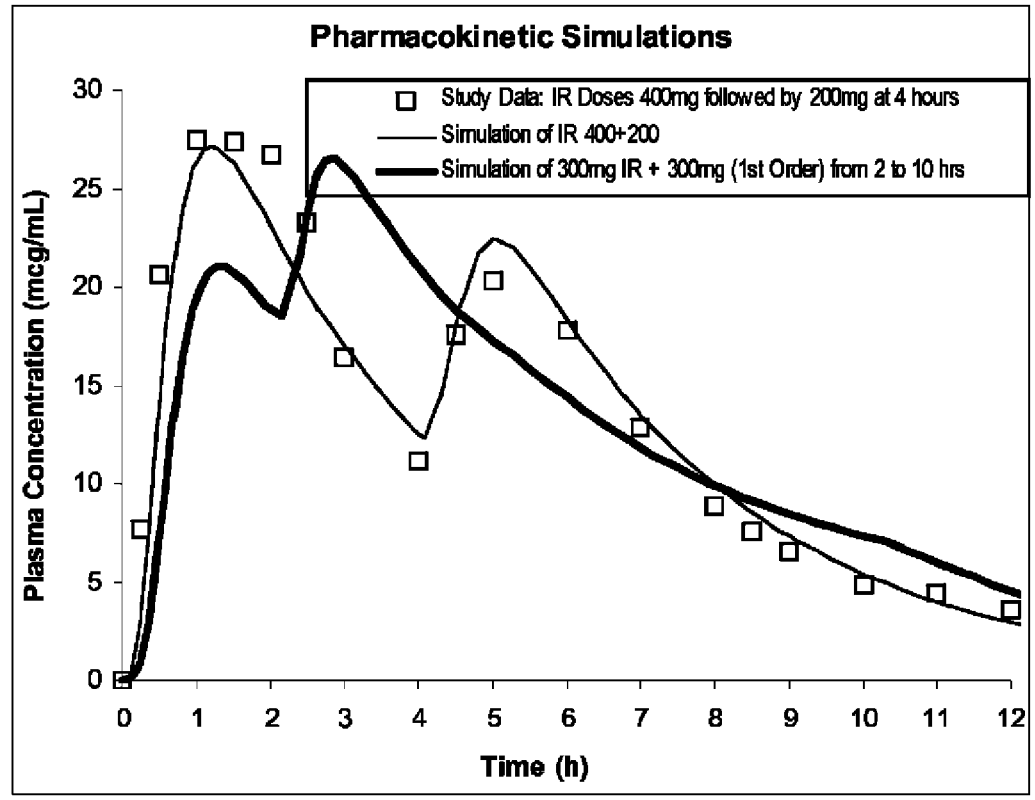
Figure 3:
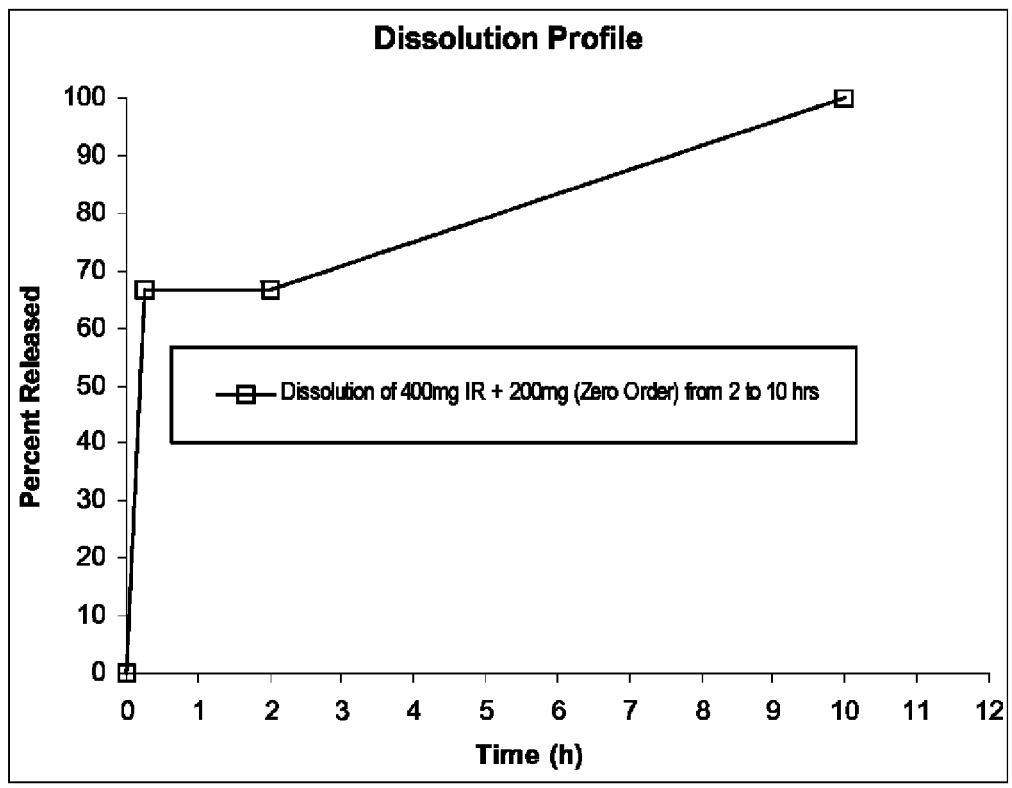
FIGS. 3A and 3B depict ibuprofen dissolution profile and absorption levels as a function of time for the dosing regimen reported in Example 3.
Figure 3:
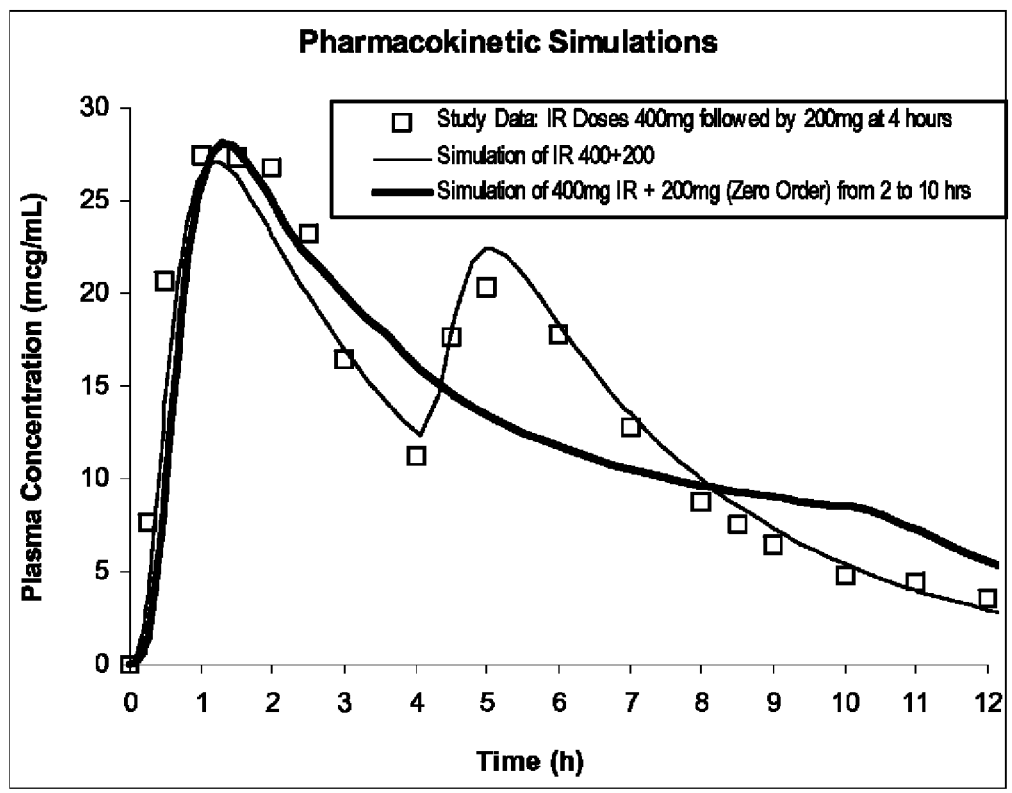
Figure 4:
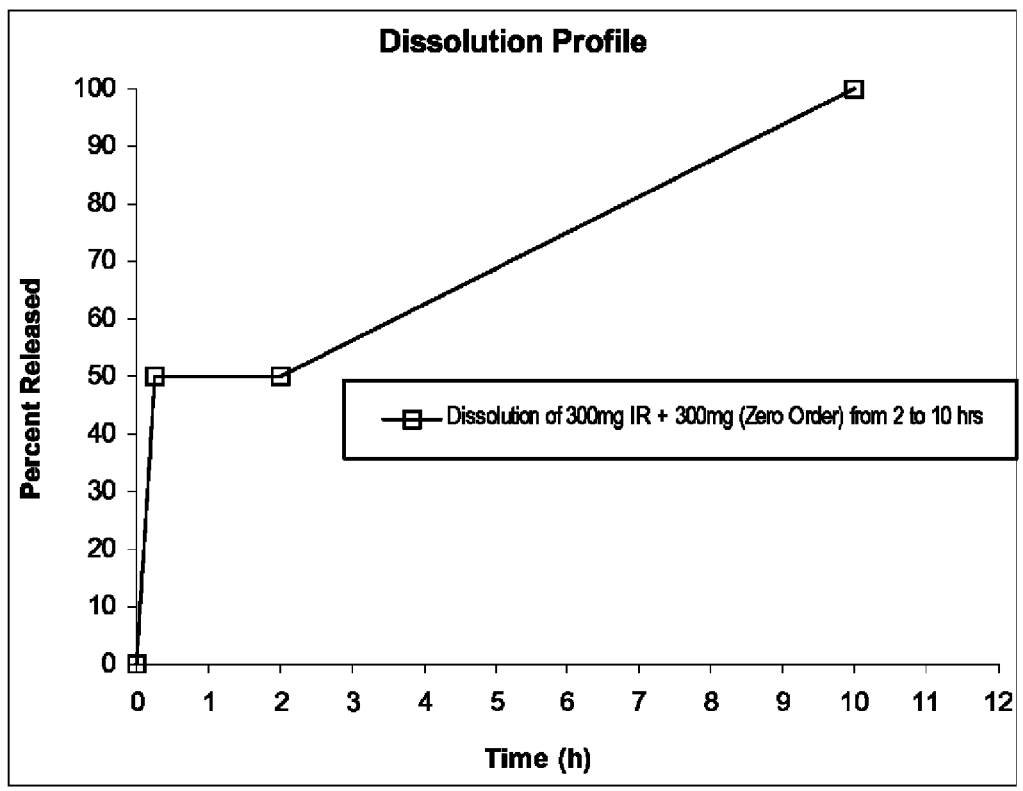
FIGS. 4A and 4B depict ibuprofen dissolution profile and absorption levels as a function of time for the dosing regimen reported in Example 4.
Figure 4:
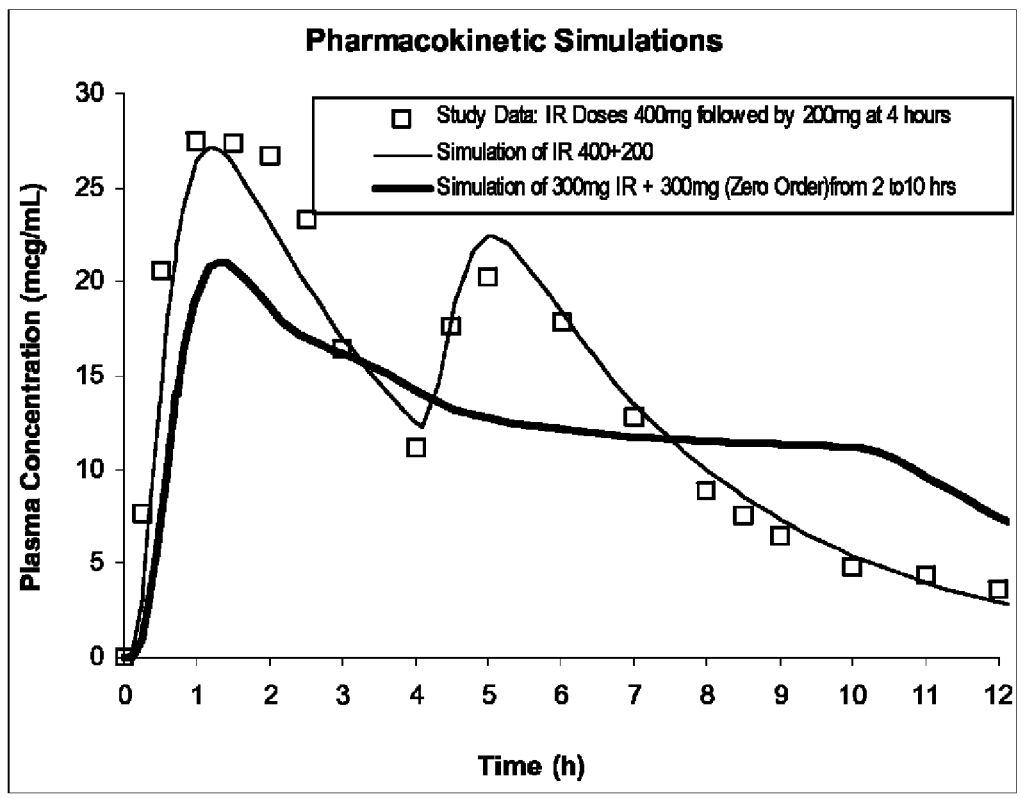

As used herein, "ATDAIRD" shall mean the "average therapeutic duration of action of an effective immediate release dose" of a particular active ingredient. For example, the typical duration of action of an immediate release dose of ibuprofen or ketoprofen is about 4 to about 6 hours. Accordingly, the ATDAIRD for ibuprofen or ketoprofen is 5 hours. The typical duration of action of an immediate release dose of Naproxen is about 8 to about 12 hours. The ATDAIRD for naproxen, therefore is 10 hours. The therapeutic duration of action of a particular active ingredient can readily be determined from the dosing instructions in the labeling for immediate release products containing that particular active ingredient.

NSAID's useful in the present invention are the propionic acid derivative NSAIDs and pharmaceutically acceptable salts of the foregoing.

In a particularly preferred embodiment, the NSAID is selected from propionic acid derivatives. Propionic acid derivatives are pharmaceutically acceptable analgesics/non-steroidal anti-inflammatory drugs having a free —CH(CH$_3$) COOH or —CH$_2$CH$_2$COOH or a pharmaceutically acceptable salt group, such as —CH(CH$_3$)COO—Na+ or CH$_2$CH$_2$COO—Na+, which are typically attached directly or via a carbonyl functionality to a ring system, preferably an aromatic ring system.

Examples of useful propionic acid derivatives include ibuprofen, naproxen, benoxaprofen, naproxen sodium, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen and bucloxic acid.

In one embodiment of the invention, the propionic acid derivative is selected from ibuprofen, ketoprofen, flubiprofen, and pharmaceutically acceptable salts and combinations thereof.

Preferably, the propionic acid derivative is ibuprofen, 2-(4-isobutylphenyl)propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

According to the invention, the NSAID is provided to a mammal in need of treatment, in particular pain relief treatment, in a specific dosing regimen over an extended time period, preferably over a 12 hour period. At time zero, a single dosing step containing an initial dose of the NSAID is provided, i.e. administered, to the mammal that also provides a second sustained release dose of the NSAID. No further NSAID is administered for the remainder of the time period.

The second dose step provides a sustained release of pharmaceutical active. The sustained release can be, for example, zero-order or first order. Zero-order release is one variation of sustained or controlled release drug system, which produces steady-state drug release over time such that the drug releases in a constant plasma profile. A first-order drug release is where the rate of elimination of drug from plasma is proportional to the plasma concentration. In certain embodiments the second dose has a lag time where drug is released from the second dose at about 1 hour, 1.5 hours 2 hours, 2.5 hours 3 hours, 3.5 hours or 4 hours.

The initial dose of NSAID may be, for example, in the range of about 0.10 to about 15 mg/kg, and the second sustained release dose may be, for example, in the range of about 0.05 to about 7.5 mg/kg, wherein the "kg" refers to the weight of the subject receiving the dose. In one embodiment, the initial dose of NSAID is at least about twice the second dose of NSAID. In certain embodiments of the invention wherein ibuprofen is employed, the initial dose is from about 400 to about 800 mg, or from about 5.7 to about 12 mg/kg, and the second sustained release dose is from about 200 to about 300 mg, or from about 2.9 to about 4.3 mg/kg. In another embodiment the initial dose of ibuprofen is from about 300 to 600 mg, or from about 4.3 to about 8.6 mg/kg, and the second sustained release dose is from about 300 to 600 mg, or from about 4.3 to about 8.6 mg/kg. In another embodiment, the initial dose and the second dose deliver approximately the same amount of active ingredient.

In one particular embodiment of the invention wherein ibuprofen is employed, the initial dose is about 400 mg, or about 5.7 mg/kg, and the second sustained release dose is about 200 mg, or about 2.9 mg/kg. Moreover, the initial dose in such embodiment is within the therapeutic range for the particular active ingredient employed, and is about twice the level of the second dose, which is also within the therapeutic range for the particular active ingredient employed. In another particular embodiment of the invention wherein ibuprofen is employed, the initial dose is about 300 mg, or about 4.3 mg/kg, and the second sustained release dose is also about 300 mg, or about 4.3 mg/kg.

In a preferred embodiment of the invention, a propionic acid derivative is administered to a mammal over a 12 hour time period, by first providing in a single dosing step to the mammal an initial dose of the propionic acid derivative at the beginning of the 12 hour time period that also provides a second sustained release dose of the propionic acid derivative, wherein the initial dose is at least about twice the second dose. No further propionic acid derivative is provided during the 12 hour time period.

In certain embodiments, the invention provides a first peak plasma concentration within the therapeutic range for the particular active ingredient employed within about 0.5 times the ATDAIRD for the active ingredient after administration of the initial dose, and a second plasma concentration within the therapeutic range for the particular active ingredient employed between about 0.8 to about 1.2 times the ATDAIRD after administration of the initial dose. In one embodiment, the plasma concentration of NSAID at about 2 times the ATAIRD after administration of the initial dose is below the known therapeutic range for the particular active ingredient employed.

In certain particular embodiments, in which the active ingredient has an ATDAIRD of about 5 hours, the invention provides a first peak plasma concentration within the therapeutic range for the particular active ingredient employed about 10 to about 30 minutes after administration of the initial dose, and a second plasma concentration within the therapeutic range for the particular active ingredient employed between about 2 to about 6 hours, alternatively between about 2 to about 8 hours after administration of the initial dose. In one embodiment, the plasma concentration of NSAID at about 10 hours after administration of the initial dose is below the known therapeutic range for the particular active ingredient employed.

In certain particular embodiments wherein ibuprofen is employed, the invention provides a first peak plasma concentration of ibuprofen of about 20 to about 30 mcg/mL in the mammal about 30 to about 120 minutes after administration of the initial dose, and a second plasma concentration of ibuprofen of about 10 to about 30 mcg/mL from about 3 to about 6 hours after administration of the initial dose. In another particular embodiment wherein ibuprofen is employed, the invention provides a first peak plasma concentration of ibuprofen of about 20 to about 30 mcg/mL in the mammal about 30 to about 120 minutes after administration of the initial dose, and a second plasma concentration of ibuprofen of about 10 to about 30 mcg/mL from about 3 to about 8 hours after administration of the initial dose. In one embodiment, the plasma concentration of ibuprofen at about 10 hours after administration of the initial dose is less than about 10 mcg/mL. In another embodiment, the plasma concentration of ibuprofen at about 6 hours after the second dose is less than about 15 mcg/mL.

The NSAID may be administered in a variety of dosage forms, for example, solid dosage forms such as tablets, coated tablets, capsules, liquid dosage forms such as syrups, and suspensions, preferably in tablet form having multiple cores of NSAID with varying dissolution properties. The initial and second doses may be administered in a single dosing step. In one embodiment the initial and second doses are administered in a single dosing step, preferably a single solid dosage form. For example, such a dosage form may comprise a single dosing step comprising an immediate release portion containing the initial dose of NSAID and a sustained release portion containing the second dose of NSAID or acetaminophen. Such a single solid dosage form may be a multilayer tablet where the first immediate release dose is provided in one layer and the second sustained release dose is provided in a second layer. A single solid dosage form may also be provided in a multiparticulate tablet wherein the first immediate release dose is provided in one portion of particulates and the second sustained release dose is provided in a second portion of particulates, or the like.

The initial dose meets United States Pharmacopeia (USP) specifications for immediate release tablets containing that active ingredient. For example, for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. (See USP 24, 2000 Version, 19-20 and 856 (1999)).

The pk blood profiles for various dosing regimes of the present invention were calculated using a simulation program. The PKPlus™ module portion of Gastroplus™ simulator software available from Simulations Plus, Incorporated, was first used to determine the best type of ACAT (Advanced Compartmental Absorption and Transit) model for immediate release ibuprofen dosing. Intravenous plasma data for ibuprofen was obtained from the following study, "Pharmacokinetics and absolute bioavailability after oral administration of ibuprofen lysine in man", Biopharmaceutics & Drug Disposition 11(3):265-78, April, 1990. Martin W., Koelowske G., Toberich H., Kerkman T.

Ibuprofen was dosed as either 200 mg or 400 mg of an intravenous solution over a 5-minute infusion time. Plasma concentration for the following time points was inputted into the PK Plus module in hours; 0.0, 0.017, 0.033, 0.05, 0.067, 0.1, 0.167, 0.333, 0.5, 0.667, 1.0, 1.5, 2.0, 3.0, 4.0, 6.0, 8.0. Plasma concentration vs. time data were extracted using summary graphs from UN-SCAN-IT™ graph digitizing software available from Silk Scientific Inc. The PK Plus module portion estimated pharmacokinetic parameters and performed calculations for the goodness of fit and Akaike Information Criterion for Noncompartment, One-Compartment, Two-Compartment and Three-Compartment Models. Based on the lowest Akaike information criterion value, the two and three-compartment model were selected as having the best fit.

Once the pharmacokinetic models were obtained based on the above information, the absorption model based on oral dosing was selected. Based on these models, simulated plasma concentration (Cp) vs. time curves were derived for three immediate release treatments; three doses of 200 mg of Ibuprofen each at 4 hours apart; a single dose of 600 mg Ibuprofen and a 400 mg dose followed by a 200 mg dose 4 hours later. Upon inspection of the curves, it was determined that the three-compartment model conferred only a very slight advantage of fit, and two compartment linear pharmacokinetic models were considered.

Several different screens within the Gastroplus™ software were modified to generate the optimum dosing curves. The Compound screen has the following parameters which can be varied:
Dosage Form: Multiple Mixed Doses
Initial Dose (mg): 400 (example)
Subsequent Doses (mg): 200 (example)
Dosing Intervals (hours): 4
Dose Volumes (mL): 250
pH for ref. Solubility: 1
Solubility (mg/mL @ pH=7): 1
Mean Precipitation Time (sec): 900
Drug Particle Density (g/mL): 1.2
Effective Particle radius (μ): 25
Diffusion Coefficient (cm2×$10^5$)=0.9388
Peff-Effective Permeability (cm/s×104): 10
Molecular Weight=206.28
Reference Log D=3.72 @ pH=1

The Physiology Screen in Gastroplus™ has the following parameters which can be varied:
Stomach: Effective Permeability=10; pH=6.70; Transit Time (hours)=0.25
Duodenum: Effective Permeability=10; pH=6.00; Transit Time (hours)=0.47
Jejunum 1: Effective Permeability=10; pH=6.20; Transit Time (hours)=0.47
Jejunum 2: Effective Permeability=10; pH=6.40; Transit Time (hours)=0.47
Ileum 1: Effective Permeability=10; pH=6.60; Transit Time (hours)=0.47
Ileum 2: Effective Permeability=10; pH=6.80; Transit Time (hours)=0.47
Ileum 3: Effective Permeability=10; pH=7.20; Transit Time (hours)=0.47
Ileum 4: Effective Permeability=10; pH=7.50; Transit Time (hours)=0.47
Colon: Effective Permeability=10; pH=5.00; Transit Time (hours)=18.00 The Pka Table screen in Gastroplus™ calculates a pH solubility of the compound of reference depending on the added pKa value.

Based on these simulations, the optimized clearance and micro-constants were derived using a human-fasted GI model. The fraction of ibuprofen unbound in plasma was set at 1.5% and the optimum clearance value was 0.04789 liters/hour/kg based on human body weight.

The following examples further illustrate the invention, but are not meant to limit the invention in any way.

EXAMPLES 1-4

The figures shown above were derived from simulated dissolution curves. A typical dissolution for ibuprofen tablets uses a USP #2 apparatus (paddles), rotating at 50 RPM, in 900 mL of pH 7.2 phosphate buffer at 37° C. The phosphate buffer is prepared by dissolving 6.067 g of anhydrous potassium phosphate dibasic and 2.067 g of anhydrous potassium phosphate monobasic in 800 mL of deionized water. It is then diluted to 1000 mL with deionized water and mixed thoroughly. Approximately 10 milliliter samples are pulled from the dissolution vessel at various timepoints (indicated in the graphs) and analyzed on a high pressure liquid chromatograph fitted with a Waters μ-Bondapak® C-18 column, and UV detector set at 254 nm. The flow rate is 2.0 mL/min The injection volume is 100 micro-liters. The mobile phase is acetonitrile and 0.1M acetic acid prepared in a ratio of 55:45 respectively. Each of the following examples represents a dose of 2 tablets per dose.

Example 1

Ibuprofen 300 mg Bi-layer Tablet (Uncoated) consisting of 200 mg immediate release (IR) layer and 100 mg sustained release (SR) layer, said tablet having a release profile with an immediate release followed by a delayed first-order release.

TABLE 1

Immediate Release Formula of Ibuprofen 200 mg

| Ingredient | % W/W | Manufacturer | Mg/Tablet |
|---|---|---|---|
| Ibuprofen Powder (Grade 115) | 94.0 | Albemarle Corp., Orangeburg, SC | 200.0 |
| Croscarmellose Sodium (Ac-Di-Sol ®) | 5.50 | FMC Corp. Newark, DE | 11.7 |
| FD&C Yellow #6 | Trace | Colorcon West Point, PA | |
| Magnesium Stearate | 0.50 | Mallinckrodt Inc., St. Louis, MO | 1.10 |
| Total (mg) | | | 212.8 |

TABLE 2

Sustained Release Formula of Ibuprofen 100 mg

| Ingredient | % W/W | Manufacturer | Mg/Tablet |
|---|---|---|---|
| Ibuprofen Powder (Grade 115) | 29.5 | Albemarle Corp. Orangeburg, SC | 100.0 |
| Lactose (Fast Flow) | 31.0 | Foremost Farms Baraboo, WI | 105.09 |
| Hydroxypropyl-methylcellulose (HPMC K4M, CR Grade) | 13 | The Dow Chemical Company, Midland, MI | 44.07 |
| Hydroxypropyl-cellulose (HPC EXF) | 26 | Aqualon (Division of Hercules Inc.) Wilmington, DE | 88.13 |
| FD&C Red # 40 | Trace | Colorcon West Point, PA | |
| Magnesium Stearate | 0.50 | Mallinckrodt Inc., St. Louis, MO | 1.69 |
| Total (mg) | | | 338.98 |

The dosage form is made as follows with ingredients from TABLE 1 and TABLE 2.

Blending:
(a) The ibuprofen powder, croscarmellose sodium and FD&C yellow #6 (TABLE 1) are de-lumped individually through a #40 mesh sieve.
(b) The delumped ibuprofen powder, croscarmellose sodium and FD&C yellow #6 from (a) are mixed in a suitable v-blender for 15 minutes.
(c) The magnesium stearate (TABLE 1) is also delumped through a #40 mesh sieve and is then added to the mixture in (b) and blended for 3 minutes.
(d) The ibuprofen powder, lactose, hydroxypropylmethylcellulose, hydroxypropylcellulose and FD&C Red #40 (TABLE 2) are de-lumped through a #40 mesh sieve.
(e) The delumped ibuprofen powder, lactose, hydroxypropylmethylcellulose, hydroxypropylcellulose and FD&C Red #40 from (d) are mixed in a suitable v-blender for 15 minutes.
(f) The magnesium stearate (TABLE 2) is also delumped through a #40 mesh sieve and is then added to the mixture in (e) and blended for 3 minutes.

Tabletting:
(1) The final blend from (f) is weighed (338.98 mg) and slightly tapped manually with an upper punch (⅜") inside the die to form a $1^{st}$ pre-compressed layer.
(2) The final blend from (c) is also weighed (212.8 mg) and loaded onto the top of the $1^{st}$ layer inside the die to form the $2^{nd}$ layer.
(3) The Bi-Layer Tablet (551.78 mg) is made at 3000 lbs compression force in a Carver Press (Menomonee Falls, Wis.) equipped with ⅜" round, shallow concave tooling sets.

Example 2

Ibuprofen 300 mg Bi-layer Tablet (Uncoated) consisting of 150 mg IR layer and 150 mg SR layer, said tablet having a release profile with an immediate release followed by a first-order release.

TABLE 3

Immediate Release Formula of Ibuprofen 150 mg

| Ingredient | % W/W | Manufacturer | Mg/Tablet |
|---|---|---|---|
| Ibuprofen Powder (Grade 115) | 70.0 | Albemarle Corp., Orangeburg, SC | 150.0 |
| Croscarmellose Sodium (Ac-Di-Sol ®) | 5.50 | FMC Corp. Newark, DE | 11.8 |
| Microcrystalline Cellulose (Avicel PH 101) | 24.0 | FMC Corp. Newark, DE | 51.4 |
| FD&C Yellow #6 | Trace | Colorcon West Point, PA | |
| Magnesium Stearate | 0.50 | Mallinckrodt Inc., St. Louis, MO | 1.10 |
| Total (mg) | | | 214.3 |

TABLE 4

Sustained Release Formula of Ibuprofen 150 mg

| Ingredient | % W/W | Manufacturer | Mg/Tablet |
|---|---|---|---|
| Ibuprofen (grade 115) | 44.0 | Albemarle Corp. Orangeburg, SC | 150.0 |
| Lactose (Fast Flow) | 16.5 | Foremost Farms Baraboo, WI | 56.25 |
| Hydroxypropyl-methylcellulose (HPMC K4M, CR Grade) | 13 | The Dow Chemical Company, Midland, MI | 44.32 |
| Hydroxypropyl-cellulose (HPC EXF) | 26 | Aqualon (Division of Hercules Inc.) Wilmington, DE | 88.64 |
| FD&C Red # 40 | Trace | Colorcon West Point, PA | |

TABLE 4-continued

Sustained Release Formula of Ibuprofen 150 mg

| Ingredient | % W/W | Manufacturer | Mg/Tablet |
|---|---|---|---|
| Magnesium Stearate | 0.50 | Mallinckrodt Inc., St. Louis, MO | 1.70 |
| Total (mg) | | | 340.91 |

Blending:
(a) The ibuprofen powder, croscarmellose sodium and, microcrystalline cellulose and FD&C yellow #6 (TABLE 3) are de-lumped individually through a #40 mesh sieve.
(b) The de-lumped ibuprofen powder, croscarmellose sodium, microcrystalline cellulose and FD&C yellow #6 from (a) are mixed in a suitable v-blender for 15 minutes.
(c) The magnesium stearate (TABLE 3) is also delumped through a #40 mesh sieve and is then added to the mixture in (b) and blended for 3 minutes.
(d) The ibuprofen powder, lactose, hydroxypropylmethylcellulose, hydroxypropylcellulose and FD&C Red #40 (TABLE 4) are de-lumped through a #40 mesh sieve.
(e) The delumped ibuprofen powder, lactose, hydroxypropylmethylcellulose, hydroxypropylcellulose and FD&C Red #40 from (d) are mixed in a suitable v-blender for 15 minutes.
(f) The magnesium stearate (TABLE 4) is also delumped through a #40 mesh sieve and is then added to the mixture in (e) and blended for 3 minutes.

Tabletting:
(1) The final blend from (f) is weighed (340.91 mg) and slightly tapped manually with an upper punch (⅜") inside the die to form a $1^{st}$ pre-compressed layer.
(2) The final blend from (c) is also weighed (214.3 mg) and loaded onto the top of the $1^{st}$ layer inside the die to form the $2^{nd}$ layer.
(3) The Bi-Layer Tablet (555.21 mg) is made at 3000 lbs compression force in a Carver Press (Menomonee Falls, Wis.) equipped with ⅜" round, shallow concave tooling sets.

Example 3

Ibuprofen 300 mg Bi-Layer Coated Tablet consisting of 200 mg IR layer and 100 mg SR layer, said tablet has a release profile with an immediate release followed by a delayed zero-order release.

TABLE 5

Immediate Release Formula of Gelatin Coating Solution

| Ingredient | % W/W | % Solid | Manufacturer |
|---|---|---|---|
| Gelatin (275 Bloom) | 30 | 100 | KIND & KNOX Sioux City, IA |
| Water | 70 | | |
| Total | 100 | 100 | |

Step A: Preparation of Gelatin Coating Solution (TABLE 5)
1. A suitable beaker is submerged in a 75° C. water bath.
2. Water is added to the beaker and let the water temperature equilibrate.
3. Gelatin is slowly dispersed into the beaker and the mixer is kept stirring until the entire gelatin dissolved.

4. The gelatin solution is placed in a 60° C. oven for 12 hours.

TABLE 6

Sustained Release Formula of Polymeric Coating Dispersion

| Ingredient | % W/W | % Solid | Manufacturer |
|---|---|---|---|
| Gellan Gum, LT 100 | 0.53 | 3.38 | Kelco Biopolymer Tadworth, Surrey KT20 5HQ, UK |
| Gelcarin GP 812 | 2.43 | 15.49 | FMC Corp. Newark, DE |
| Hydroxypropyl-methylcellulose (HPMC K4M, CR Grade) | 12.73 | 81.13 | The Dow Chemical Company, Midland, MI |
| Water | 84.30 | | |
| Total | 100.00 | 100.00 | |

Step B: Preparation of Polymeric Coating Dispersion (TABLE 6)
1. A suitable beaker is submerged in a 90° C. water bath.
2. Water is added to the beaker and let the water temperature equilibrate. Maintain the temperature at 90° C. throughout the whole preparation processes.
3. Gellan Gum, LT 100 is slowly dispersed into the beaker and the mixer is kept stirring until dissolved.
4. Gelcarin GP 812 is slowly dispersed into the beaker and the mixer is kept stirring until dissolved.
5. HPMC is slowly dispersed into the beaker and the mixer is kept stirring until well dispersed.

The Bi-Layer Tablet obtained from EXAMPLE 1 is coated with polymer solution from TABLE 6 around the SR bottom layer ($2^{nd}$ layer prepared from TABLE 2) and gelatin solution from TABLE 5 around the IR top layer ($1^{st}$ layer prepared from TABLE 1). This achieves a dosage form with burst release followed by a zero-order release.

Example 4

Ibuprofen 300 mg Bi-layer Tablet consisting of 150 mg IR layer and 150 mg SR layer, said tablet has a release profile with an immediate release followed by a delayed zero-order release.

The Bi-Layer Tablet obtained from EXAMPLE 2 is coated with polymer solution from TABLE 6 around the SR bottom layer ($2^{nd}$ layer prepared from TABLE 4) and gelatin solution from TABLE 5 around the IR top layer ($1^{st}$ layer prepared from TABLE 3). This achieves a dosage form with burst release followed by a zero-order release.

Part I: Tablet Coating Procedure (EXAMPLE 3 & EXAMPLE 4)

A laboratory scale thermal cycle molding unit having a round shape of dimension of ⅜", is used to apply the shell portion to the Bi-Layer Tablet core. The molding unit comprises a single mold assembly made from an upper mold assembly portion comprising an upper mold cavity, and a lower mold assembly portion comprising a lower mold cavity. Two sets of coated tablets are prepared as described in EXAMPLE 3 and EXAMPLE 4. The Bi-Layer Tablet core prepared as described in EXAMPLE 1 or EXAMPLE 2 is inserted into the cavity. The lower mold assembly portion is first cycled to a hot stage at 90° C. for 2 minutes. The coating solution of polymeric coating (TABLE 6), which is prepared as described in Step B, is injected into the lower mold cavity to coat the SR layer portion (TABLE 2 or TABLE 4) of said tablet.

A blank upper mold assembly portion is mated with the lower mold assembly portion. The mold assembly is then cycled to a cold stage at 2° C. for 60 seconds to harden the first coating portion. The blank mold assembly portion is removed from the lower mold assembly portion. The upper mold assembly portion is cycled to a hot stage at 90° C. for 2 minutes.

The lower mold assembly portion, which has been maintained at 2° C., is mated with the upper mold assembly portion in such a way that the core of EXAMPLE 1 or EXAMPLE 2 is mated with the first core station of the upper mold assembly.

The gelatin coating solution (TABLE 5), which is prepared and described in Step A is injected into the upper mold portion and covers the IR layer portion (TABLE 1 or TABLE 3) of the tablet cores. The upper mold assembly portion is then cycled to a cold stage at 2° C. for 90 seconds to harden the second coating portion. The lower mold assembly portion is then removed and the finished dosage form, a molded tablet coated with two halves of the 2 coating materials, is ejected from the upper mold cavity. The weight gain from the coating material (i.e. the difference in weight between the finished dosage form and the core) is recorded. The coated tablets are then dried at 50° C. in an oven for 24 hours.

We claim:

1. A method of reducing fever over a 12 hour period, comprising administering to a mammal in need thereof a dosage form comprising an immediate release portion comprising about 200 mg to about 400 mg of an immediate release dose of ibuprofen, wherein said immediate release dose is released at the beginning of said 12 hour period, and a sustained release portion comprising about 100 mg to about 200 mg of a sustained release dose of said ibuprofen, wherein said sustained release dose is released at about 2 hours to about 10 hours after release of said immediate release dose, and wherein said immediate release portion contains a dose that is at least about twice the dose in the sustained release portion.

2. The method of claim 1, wherein said ibuprofen has a duration of therapeutic effect which lasts at least about 6 hours after release of said sustained release dose.

3. The method of claim 1, wherein the sustained release dose is zero-order.

4. The method of claim 1, wherein the sustained release dose is first-order.

5. The method of claim 1, wherein said immediate release dose provides about 5.7 mg/kg to about 12 mg/kg of ibuprofen and said sustained release dose provides about 2.5 mg/kg to about 4 mg/kg of ibuprofen.

6. The method of claim 1, wherein said immediate release dose provides about 5.7 mg/kg of ibuprofen and the sustained release dose provides about 2.86 mg/kg of ibuprofen.

* * * * *